United States Patent [19]
Gregory

[11] Patent Number: 5,903,117
[45] Date of Patent: May 11, 1999

[54] METHOD AND ADAPTOR FOR CONNECTING A POWERED SURGICAL INSTRUMENT TO A MEDICAL CONSOLE

[75] Inventor: William W. Gregory, Jacksonville, Fla.

[73] Assignee: Xomed Surgical Products, Inc., Jacksonville, Fla.

[21] Appl. No.: 08/959,027

[22] Filed: Oct. 28, 1997

[51] Int. Cl.[6] .................................................. H02K 23/00
[52] U.S. Cl. .......................... 318/254; 318/138; 318/439
[58] Field of Search .................................. 318/254, 3, 4, 318/767, 768, 439

[56] References Cited

U.S. PATENT DOCUMENTS

| 5,602,449 | 2/1997 | Krause et al. | 318/254 |
| 5,640,073 | 6/1997 | Ikeda et al. | 318/439 |
| 5,773,941 | 6/1998 | Moritz et al. | 318/254 |
| 5,804,936 | 9/1998 | Brodsky et al. | 318/254 |

*Primary Examiner*—William M. Shoop, Jr.
*Assistant Examiner*—Rita Leykin

[57] ABSTRACT

A brush-to-brushless motor controller adapter for use with a two-wire output signal from a medical console consists of a small enclosure containing a circuit board and has a short cable terminating in a two-wire connector which plugs into the two-wire controller output of the medical console and a connector jack for an electrical connection to a surgical instrument having a brushless D.C. motor. The brush-to-brushless motor controller generates a stable voltage for the adapter internal electronics (i.e., 12 to 15 volts), from a varying input voltage (i.e., 2.5 to 30 volts D.C.). The surgical instrument brushless D.C. motor speed is controlled as a function of the console output signal drive voltage amplitude and the adapter accepts pulsed inputs from a high power two-wire motor controller (e.g., 10 watts and up). The adapter accepts bipolar drive signals and is adapted to reverse the surgical instrument brushless D.C. motor direction in response to a change in input voltage polarity from the two-wire medical console controller circuit. The adapter circuit of the present invention eliminates the need for a negative supply voltage by creating a positive bias in the control loop such that the control signal is nominally 2.5V above ground (i.e., zero volts) and the adapter internal positive voltage supply level. The adapter may be calibrated to provide a given top motor speed for different consoles by adjusting speed gain and speed offset voltages and so can work with consoles having different maximum speed voltage signals. The instrument including the brushless D.C. motor is preferably, but not necessarily, a surgical instrument such as a shaver or resector and may be used in conjunction with ancillary equipment such as a selectively switchable pump.

19 Claims, 8 Drawing Sheets

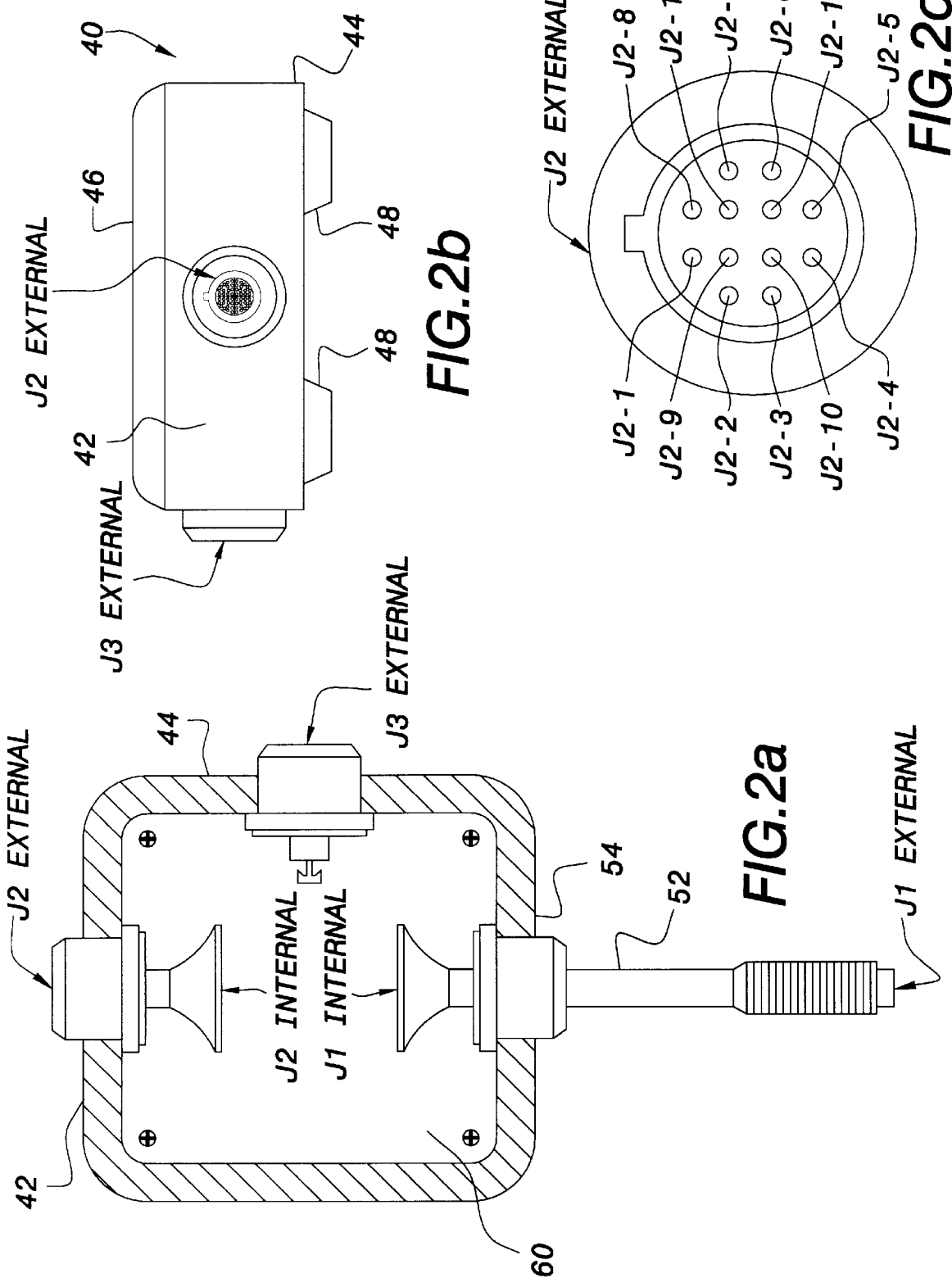

HUMMER ADAPTER WIRING DIAGRAM

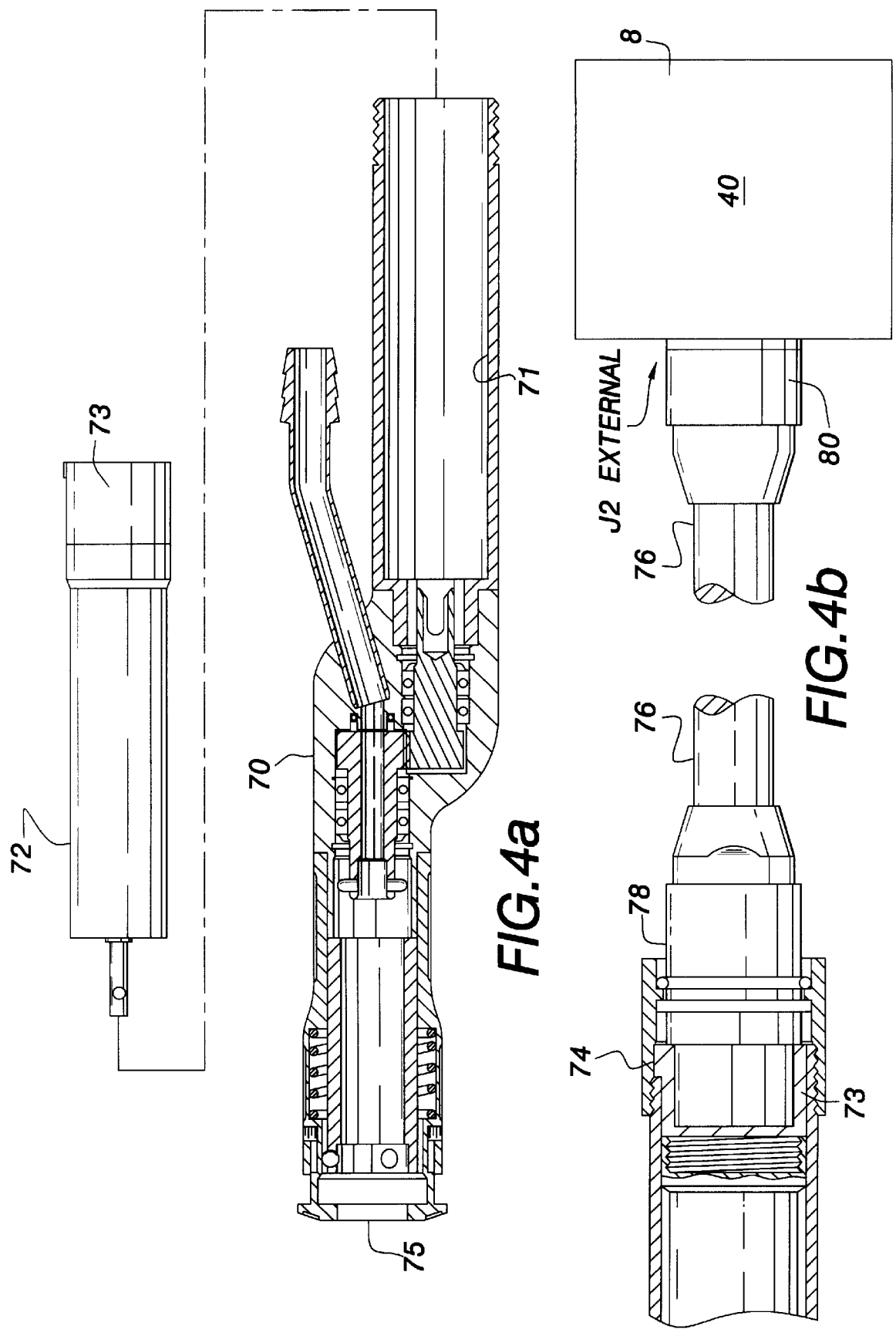

METHOD AND ADAPTOR FOR CONNECTING A POWERED SURGICAL INSTRUMENT TO A MEDICAL CONSOLE

BACKGROUND OF THE INVENTION

1. Field of the Invention

The present invention relates to a method for connecting a surgical instrument to a medical console and, more particularly, to an electrical adapter for connecting a new surgical instrument having a brushless direct current (D.C.) motor to an existing medical console having a two-wire controller designed for connection to brushes in a commutated D.C. motor.

2. Discussion of the Related Art

Brushless D.C. motors are becoming commonplace in many medical applications, especially ear, nose and throat (ENT) surgery, due to advantages such as increased reliability, increased life expectancy and reduced radio frequency emissions or interference (RFI). Brushless motors do not include parts associated with mechanical commutation (e.g., brushes) and so arcing is eliminated. One difficulty encountered in using brushless D.C. motors in surgical instruments, such as shavers, is that many of the medical consoles presently in use in hospitals and other medical facilities have controller circuits adapted for use with two-wire, commutated D.C. motors, and replacement of existing medical consoles would require an unacceptable expense. Medical consoles with two-wire controllers apply voltage in one of two possible polarities. For a first polarity, the commutated D.C. motor spins clockwise (CW) and with the opposite polarity voltage applied, the motor spins counter clockwise (CCW).

Brushless D.C. motors do not have brushes to commutate the motor, and a motor controller for use with brushless D.C. motors must sense the position of the motor rotor and commutate (i.e., control the direction and position) the motor electronically. Accordingly, the brushless motor controllers of the prior art are incompatible with and more complex than the two-wire motor controllers used in the existing medical consoles.

In the past, the high RFI emissions associated with arcing brushes in commutated D.C. motors were of little concern to surgical instrument designers or users. In the modern ENT surgical facility, however, computers and a wide variety of wireless communications devices are employed and can be impaired by emissions from any device having poor RFI performance. As an example, new ENT stereotactic surgical imaging systems incorporate sensors and computers with little tolerance for RF emissions, and use of a surgical instrument with a commutated D.C. motor is more likely to compromise imaging system performance.

SUMMARY OF THE INVENTION

Accordingly, it is a primary object of the present invention to overcome the above-mentioned difficulties by providing an electrical adapter including an electrical circuit for electrically connecting a traditional two-wire controller (as is used in many medical consoles) to a surgical instrument having a brushless D.C. motor.

Another object of the present invention is providing a brush-to-brushless motor controller adapter enabling operating room personnel to use existing traditional medical consoles, thereby avoiding replacement of a familiar and expensive piece of equipment.

Yet another object of the present invention is to efficiently transferring power from a two-wire controller to a surgical instrument having a brushless D.C. motor, sensing the desired motor drive direction and controlling motor speed, and so avoiding excessive RFI in the surgical environment.

Another object of the present invention is to calibrate or adjust an adapter to accomodate various medical consoles providing various input signals.

The aforesaid objects are achieved individually and in combination and it is not intended that the present invention be construed as requiring two or more objects to be combined unless expressly required by the claims attached hereto.

The electrical adapter of the present invention permits use of a surgical handpiece having a brushless D.C. motor driving a surgical implement with a medical console of the type designed for connection to brushes in a commutated D.C. motor and, thus, provides new uses for existing consoles. A method according to the present invention includes the steps of coupling the adapter to a medical console of the type having a two-wire controller for connection to brushes in a commutated D.C. motor, connecting an output of the adapter to a brushless D.C. motor in a surgical handpiece for driving a surgical implement and controlling operation of the surgical handpiece via the medical console.

In accordance with the present invention, a brush-to-brushless motor controller adapter for use with a two-wire output signal from a medical console includes a small enclosure containing a circuit board. The adapter has a short cable terminating in a two-wire connector for plugging into the medical console two-wire controller output and an eight-wire connector for connection to an ENT surgical instrument, or the like, having a brushless D.C. motor. The brush-to-brushless motor controller adapter of the present invention generates a stable voltage for supplying the adapter circuit board (i.e., 12 to 15 volts), from the medical console two-wire output (i.e., a varying voltage of 2.5 to 30 volts D.C.). The ENT surgical instrument brushless D.C. motor speed and direction are controlled as a function of the medical console output signal's voltage amplitude and polarity, respectively, and the adapter can accept pulsed inputs from a high power two-wire motor controller (e.g., at ten or more watts). The adapter controller operates with as little as 2.5 volts D.C. input by employing Schottky diodes (for minimal rectifier loss), a step-up voltage converter circuit (for maintaining a stable supply voltage, even with an input voltage as low as 2.0 volts D.C.) and a MOSFET driving stage (the MOSFET's turn on with as little as 2.0 volts D.C. between the gate and source). The adapter contains all the electronics required for driving a three-phase brushless D.C. motor from a two-wire D.C. motor controller drive signal and has input filtering for operability with pulse width modulated, pulse frequency modulated or linear two-wire controller outputs. Commercially available brushless D.C. motor controller, three-phase brushless motor driver and D.C.-D.C. converter integrated circuits are employed to provide an economical adapter circuit of small size. The adapter is calibratable to provide a top brushless motor speed of 3000 RPM by adjusting "full speed gain" voltage and "start speed offset" voltage through adjustable resistors and so can accommodate and work when connected to medical consoles having different maximum speed voltage signals; for example, a first medical console may have an operating range of zero to twelve volts and a second console may have an operating range of zero to twenty-five volts. By adjusting the two calibration adjustable resistor settings, the adapter accommodates either console.

The adapter drive electronics transmit the entire adapter input voltage to the output drive stage P channel field effect transistors (FETs), at the gate to source junction, in order to turn on the transistors when the adapter input signal voltage is approximately 12 volts or below but reduces the gate to source drive voltage applied when the adapter input exceeds 12 volts D.C. and thus allows optimum efficiency when operating with low input voltages but limits the voltage applied to the output drive stage FET gate to source junctions to under 20 volts for adapter input voltages of up to 30 volts, an important consideration since the output drive stage P channel FETs gate-to-source junction have a maximum gate-to-source voltage ($V_{gs}$) rating of 20 volts. The adapter accepts bipolar drive signals and reverses the surgical instrument brushless D.C. motor direction in response to a change in input voltage polarity from the two-wire medical console controller circuit. The adapter circuit of the present invention eliminates the need for a negative supply voltage by creating a positive bias in the control loop such that the control signal is nominally 2.5 volts above the ground or return rail level and the adapter internal positive voltage supply rail level. Positive bias is needed in order to permit a bipolar drive signal without a negative voltage supply and so a control signal op-amp has inverting and non-inverting inputs connected between the rails (i.e., rail- to-rail) in the speed control loop of the motor controller adapter.

The electrical adapter of the present invention is designed for use in combination with a surgical instrument of the type having a handpiece housing a brushless D.C. motor for driving a surgical implement, such as shavers, resectors, burs and the like used in arthroscopic and ENT procedures. In addition, the adapter can be used to drive ancillary equipment such as a selectively switchable vacuum pump or irrigation pump.

In operation, the adapter of the present invention is connected to the two-wire controller from the console and a direction sensing circuit is used to sense the polarity of the console output and generate a direction signal. A rectifier bridge and filter are used to filter the two-wire input signal and the filtered input signal is applied to a three-phase MOSFET bridge connected directly to a surgical instrument handpiece including the brushless D.C. motor. The filtered output is also applied across an op-amp, the output of which is input to a summing circuit, along with an offset voltage, to generate a speed signal for input to a conventional three-phase motor controller circuit. The direction sensing circuit also has an input into the three-phase motor controller electronics and provides speed and direction input signals to the three-phase motor controller electronics. The three-phase motor controller electronic circuit has an output connection to the handpiece having the brushless D.C. motor. The three-phase motor controller also has an output signal selectively connectable to an auxiliary pump circuit, such that the pump can operate at a speed appropriate to operation of the brushless D.C. motor in the surgical instrument (e.g., the micro resector or shaver).

The above and still further objects, features and advantages of the present invention will become apparent upon consideration of the following detailed description of a specific embodiment thereof, particularly when taken in conjunction with the accompanying drawings, wherein like reference numerals in the various figures are utilized to designate like components.

BRIEF DESCRIPTION OF THE DRAWINGS

FIG. 2*a* is an overhead view in partial cross section of the adapter assembly.

FIG. 2*b* is a distal end view of the adapter housing of the present invention.

FIG. 2*c* is a distal end view of the adapter output electrical connector.

FIG. 4*a* is an exploded view, partly in section, of a powered handpiece for use with the adapter of the present invention.

FIG. 4*b* is a broken side view, partly in section, of a proximal portion of the handpiece and the adapter of the present invention.

DETAILED DESCRIPTION OF THE PREFERRED EMBODIMENT

Figure 1:
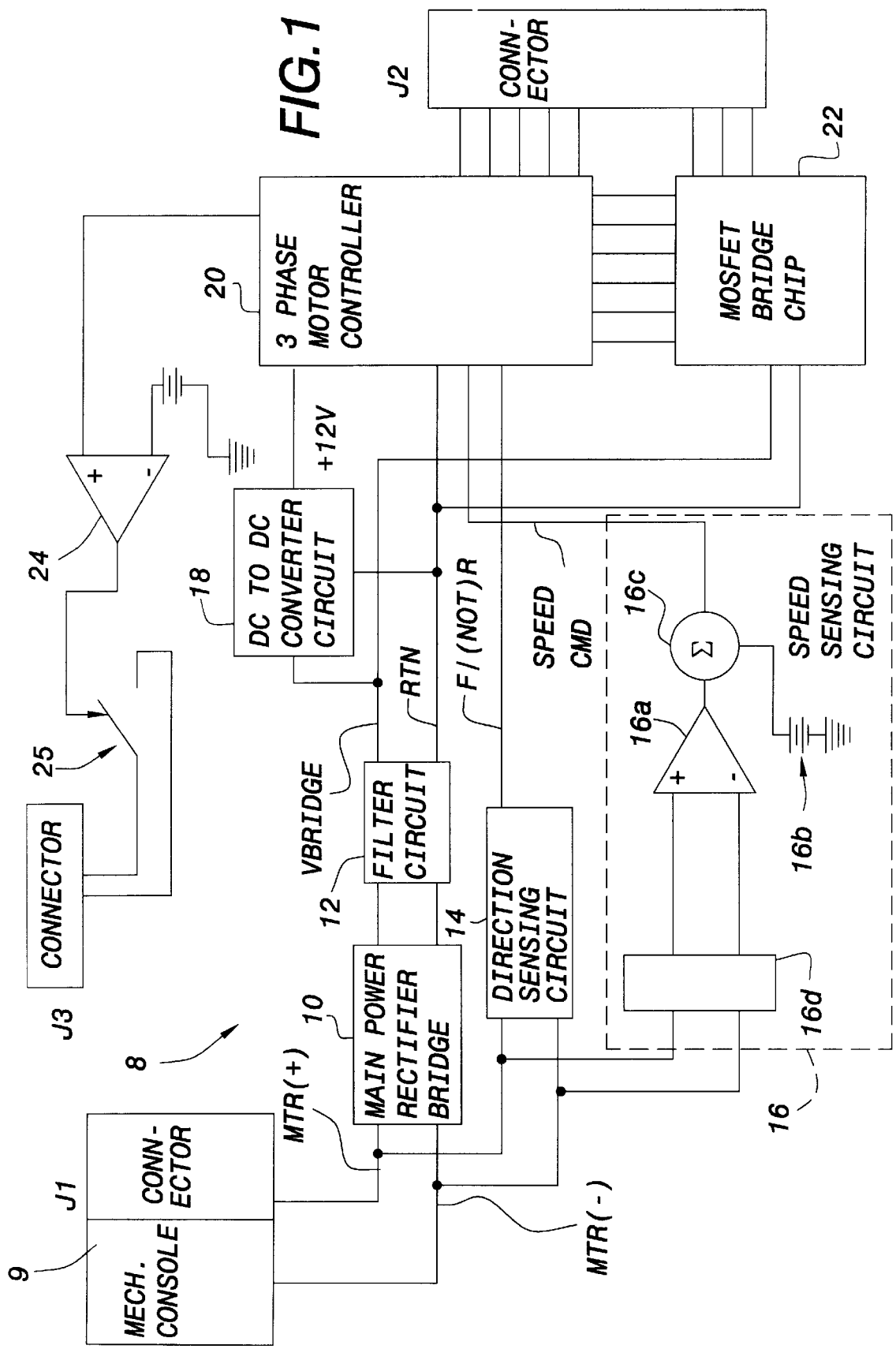
FIG. 1 is a functional block diagram of the electrical adapter of the present invention.

Referring specifically to FIG. 1 of the accompanying drawings, a functional block diagram illustrates a brush-to-brushless electrical motor control adapter 8 in accordance with the present invention, including an input electrical connector J1 for making a two-wire connection to a medical console 9. Medical console 9 provides a two-wire bipolar analog output and can be, for example, one of the Stryker Corp. models, such as the "Hummer", the "SE3", or the "SE4". Adapter connector J1 receives an input signal from the medical console and includes a first conductor MTR+ and a second conductor MTR– connected to the input of a main power rectifier bridge 10, a direction sensing circuit 14 and a speed sensing circuit 16. Rectifier bridge circuit 10 is a two-port circuit having a two-wire output connected to the input of a two-port filter circuit 12. The output of filter circuit 12 are the Vbridge and RTN (return) lines connected to the inputs of the three-phase motor controller electronics integrated circuit 20, including chip 20*a* (e.g., U7, shown in FIG. 3*c*, a Motorola (TM) MC33035) and the three-phase MOSFET bridge integrated circuit chip 22 (e.g., U8, a National Semiconductor (TM) NDM3000). Direction sensing circuit 14 has a first input connection to the MTR+ line from the J1 connector and a second input connection to the MTR– line from the J1 connector and produces an output signal indicative of forward or reverse direction "F/(not)R". The output signal of direction sensing circuit 14 is an input to the three-phase motor controller electronics chip 20*a* at pin 3 (FwdRev).

Speed sensing circuit 16 is part of a speed control loop and has a first input connection to the MTR+ line from the J1 connector and a second input connection to the MTR– line from the J1 connector via a half-bridge rectifier 16*d* providing an input to a non-inverting (+) input of a differential amplifier 16*a*. An offset voltage from a reference voltage source 16*b* is summed with the output from the differential amplifier 16*a* in summing circuit 16*c* to form the speed command output signal. The speed command output signal is input to the three-phase motor controller electronics chip 20*a* at pin 11 (Error Amp noninverting input). A DC to DC converter circuit 18 has first and second inputs across the output of filter 12 (i.e., the Vbridge and return lines). DC to DC converter circuit 18 produces a stable output supply voltage of approximately 12 volts for use in the adapter circuitry; the 12 volt supply is also provided to the three-phase motor controller electronics chip 20*a*. Three-phase motor controller electronics chip 20*a* is also connected to the three-phase MOSFET bridge chip 22 (U8) and to an output connector J2 for connection to an instrument having a three-phase brushless D.C. motor. Another output from the three-phase motor controller electronics chip 20a is a "speed out" signal provided to amplifier 24 and, via a switch 25, to a second output connector J3 for connection to an accessory such as a suction pump or the like.

Turning now to FIGS. 2a and 2b there is illustrated an overhead view and a side view, respectively, of a housing 40 having a cable terminated in an electrical connector, J1external, for connection to medical console 9. A first exterior output connector, J2external, is disposed on a first side wall 42 of housing 40 and is adapted for connection to a surgical instrument handpiece. A second exterior output connector, J3external, is situated on a second side wall 44 of housing 40 for connection to a suction pump or the like. In the example of FIGS. 2a and 2b, housing 40 is a box made of ABS plastic and having a removable top 46, has a wall thickness of 0.138 inches, a length of 2.52 inches, a width of 2.28 inches and a height of 1.38 inches. Preferably, at least three rubber feet 48 are disposed on the bottom surface 50 as illustrated in FIG. 2b for stability. A cable 52 is terminated in a four conductor electrical connector, J1external , is eight inches long (for example) and is attached via a strain relief fitting in a third side wall 54 and connected to circuit board 60 via another electrical connector, J1internal, on the interior of adapter housing 40. Similarly, as shown in FIG. 2a, J2internal is an internal PC board electrical connector wired to J2 external. Optional connector J3external is adapted for connection to an optional accessory, as described below, and is wired directly to the internal PC board of adapter 8.

Figure 2D:
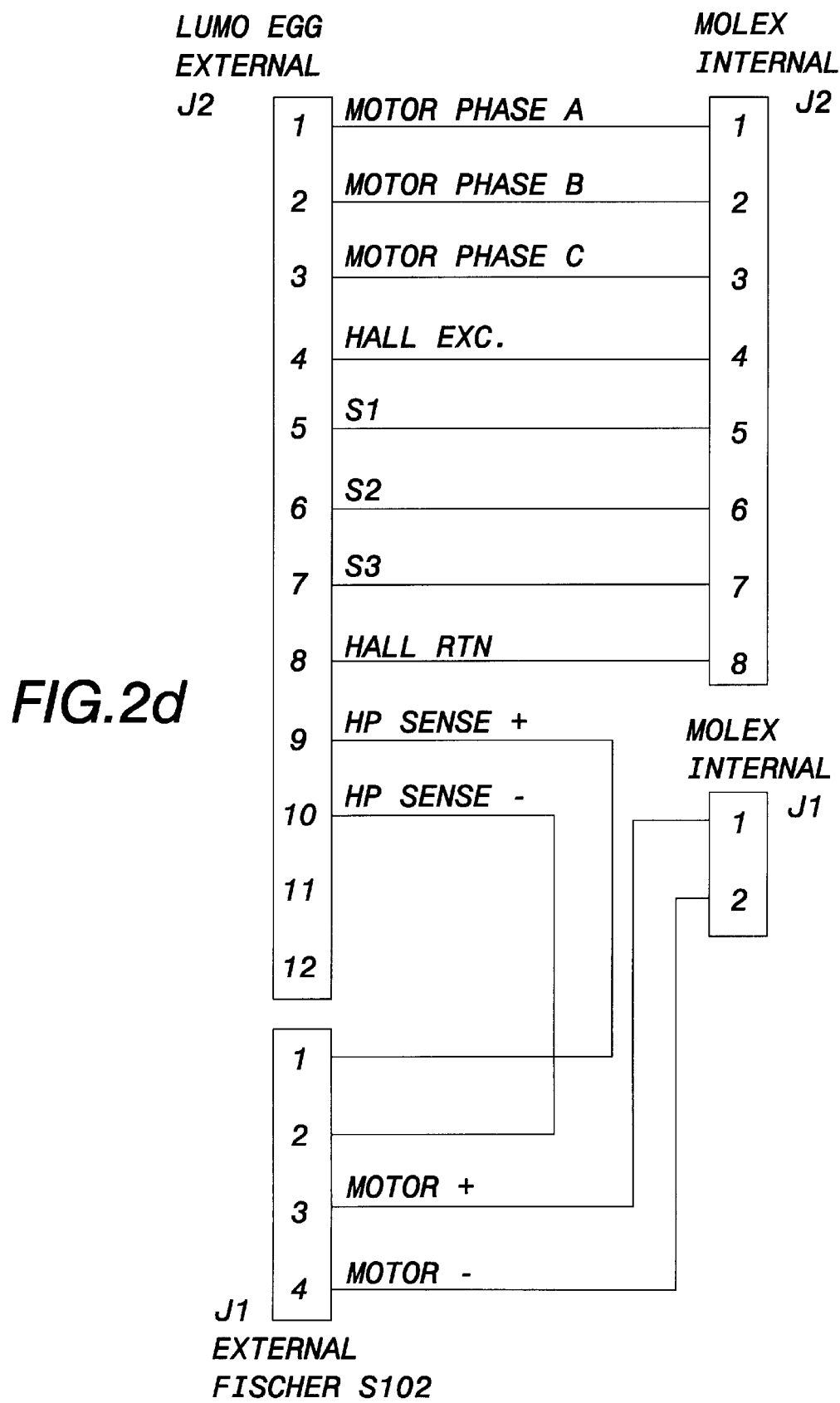
FIG. 2*d* is an internal wiring diagram of the electrical adapter of the present invention.

Turning now to FIG. 2c, a distal end view of output connector J2external shows twelve female pin receiving sockets J2-1, J2-2, J2-3, J2-4, J2-5, J2-6, J2-7, J2-8, J2-9, J2-10, J2-11 and J2-12, wired internally as shown in the wiring diagram of FIG. 2d. Specifically, pin J2-1 of the J2external (Lemo) connector is internally wired to the J2internal (Molex) connector pin 1 and is used for conducting the brushless motor phase A drive signal. Pin J2-2 of the J2external (Lemo) connector is internally wired to the J2internal (Molex) connector pin 2 and is used for conducting the brushless motor phase B drive signal. Pin J2-3 of the J2external (Lemo) connector is internally wired to the J2internal (Molex) connector pin 3 and is used for conducting the brushless motor phase C drive signal. Pin J2-4 of the J2external (Lemo) connector is internally wired to the J2internal (Molex) connector pin 4 and is used for conducting the brushless motor hall excitation signal. Pin J2-5 of the J2external (Lemo) connector is internally wired to the J2internal (Molex) connector pin 5 and is used for conducting the brushless motor first hall sensor signal. Pin J2-6 of the J2external (Lemo) connector is internally wired to the J2internal (Molex) connector pin 6 and is used for conducting the brushless motor second hall sensor signal. Pin J2-7 of the J2external (Lemo) connector is internally wired to the J2internal (Molex) connector pin 7 and is used for conducting the brushless motor third hall sensor signal. Pin J2-8 of the J2external (Lemo) connector is internally wired to the J2internal (Molex) connector pin 8 and is used for conducting the brushless motor hall sensor return signal. Pin J2-9 of the J2external (Lemo) connector is internally wired to the J1external (Fischer) connector pin 1 and is used for conducting the motor HP sense (+) signal. Pin J2-10 of the J2external (Lemo) connector is internally wired to the J1external (Fischer) connector pin 2 and is used for conducting the motor HP sense (−) signal. Pin 3 of the J1external (Fischer) connector is internally wired to the J1 internal (Molex) connector pin 1 and is used for conducting the commutated motor (+) signal. Pin 4 of the J1external (Fischer) connector is internally wired to the J1internal (Molex) connector pin 2 and is used for conducting the commutated motor (−) signal.

Turning now to FIGS. 3a–3d, there is illustrated at connector J1internal line 1 and line 2 (i.e., J1:1 and J1:2) conductors for the MTR+ and MTR− input connections to main power full-wave rectifying bridge 10 including diodes D1, D2, D3 and D4. Bridge 10 is connected in cascade with active filter circuit 12 including NPN transistor Q1 connected at its base with the cathode of 27V zener diode VR1. Zener diode VR1 is connected at its anode to ground (i.e., return). The output of filter 12 is Vbridge, a voltage not exceeding 25 volts, and is taken from the emitter of transistor Q1

Also connected to the MTR+ and MTR− signal lines is the direction sensing circuit 14 including comparator U1. The output of direction sensing circuit 14 is the F/(not)R signal and is taken from the output of comparator U1 for connection to pin 3 (FWD/REV) of three-phase motor controller electronics chip 20a, as shown traversing FIGS. 3a and 3c; see discontinuous line B.

Figure 3A:
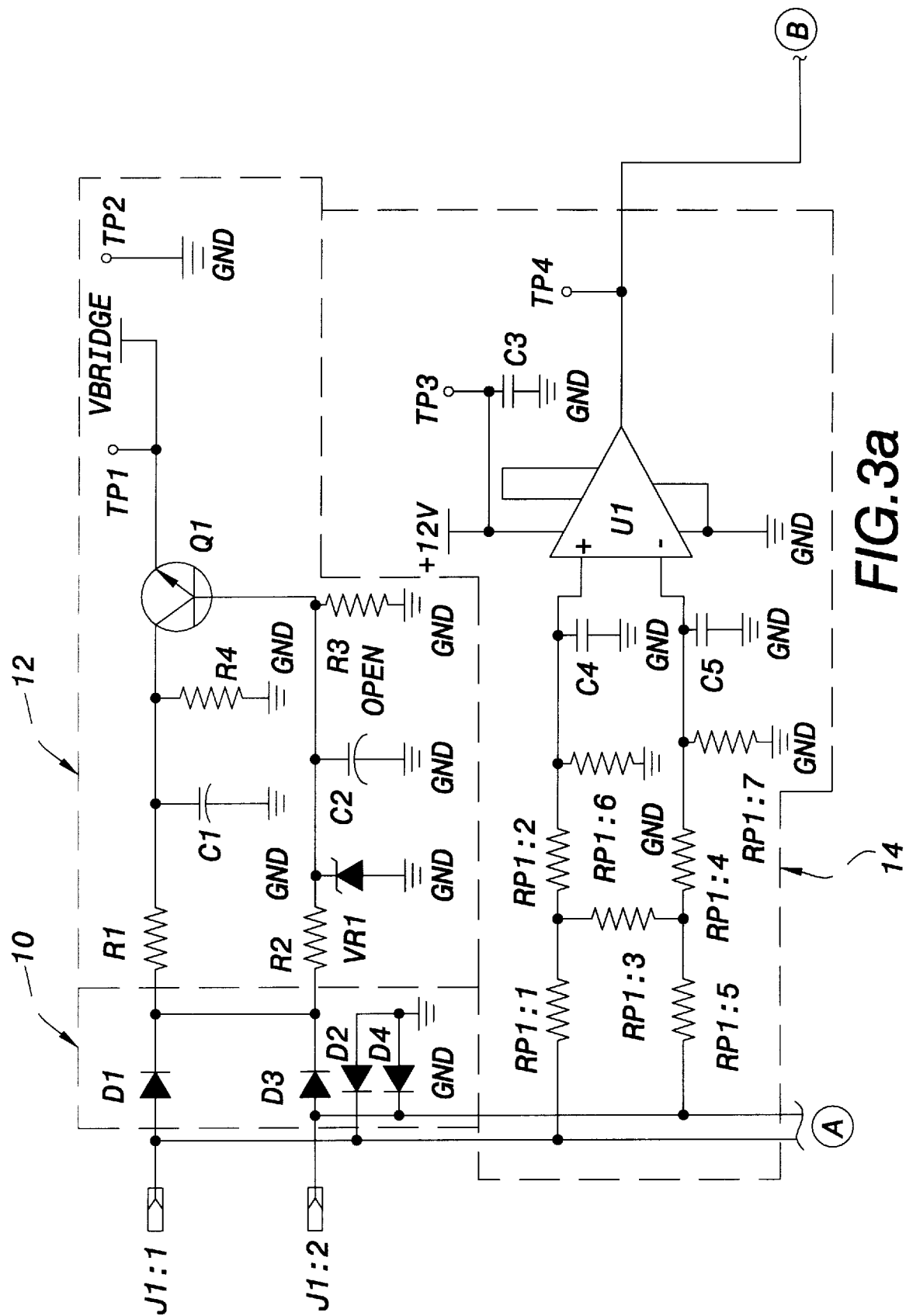
FIGS. 3*a*, 3*b*, 3*c* and 3*d* are connected segments of the electrical schematic diagram for the adapter circuit.
Figure 3B:
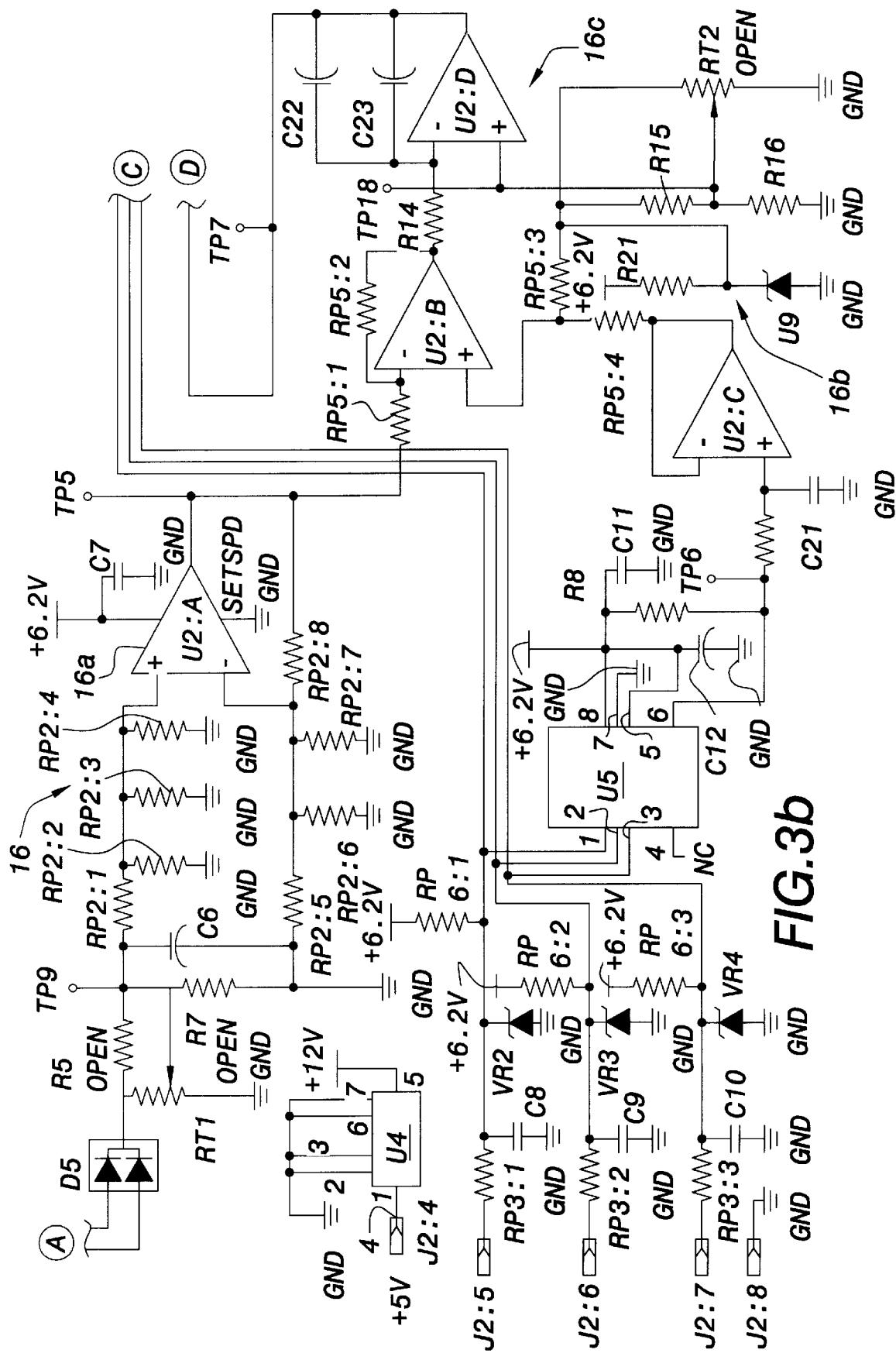

Speed sensing and control circuit 16 has inputs coupled through half bridge 16d including diode pair D5 attached to the MTR+ and MTR− lines. Differential amplifier 16a generates the input to summer circuit 16c (including op-amps U2:B, U2:C and U2:D with reference voltage source circuit 16b) for generating a speed command signal input to the three-phase motor controller electronics chip 20a at pin 11 (line "D" traversing FIGS. 3b and 3c). The speed of the brushless motor (not shown) is sensed and a speed feedback signal is received in the closed loop motor control integrated circuit U5 (e.g., a Motorola (TM) MC33039D) via connector J2 lines 5, 6 and 7 (i.e., J2:5, J2:6 and J2:7). The closed loop motor control (I.C. U5 generates a feedback signal for input to summer circuit 16c. The adapter speed sensing and control circuit 16 works in conjunction with adjustable resistors RT1 and RT2 (as shown in FIG. 3b). Adaptor 8 is calibratable to provide a maximum selected brushless motor speed (e.g., approximately 3000 RPM) by adjusting "full speed gain" voltage through adjustable resistor RT1 and "start speed offset" voltage through adjustable resistor RT2, and so can accommodate and work when connected to medical consoles having differing maximum speed voltage signals; for example, a first medical console may have an output signal operating range of zero to twelve volts and a second console may have an output signal operating range of zero to twenty-five volts. By adjusting the two calibration adjustable resistor (RT1, RT2) settings, adapter 8 accommodates either console.

Figure 3C:
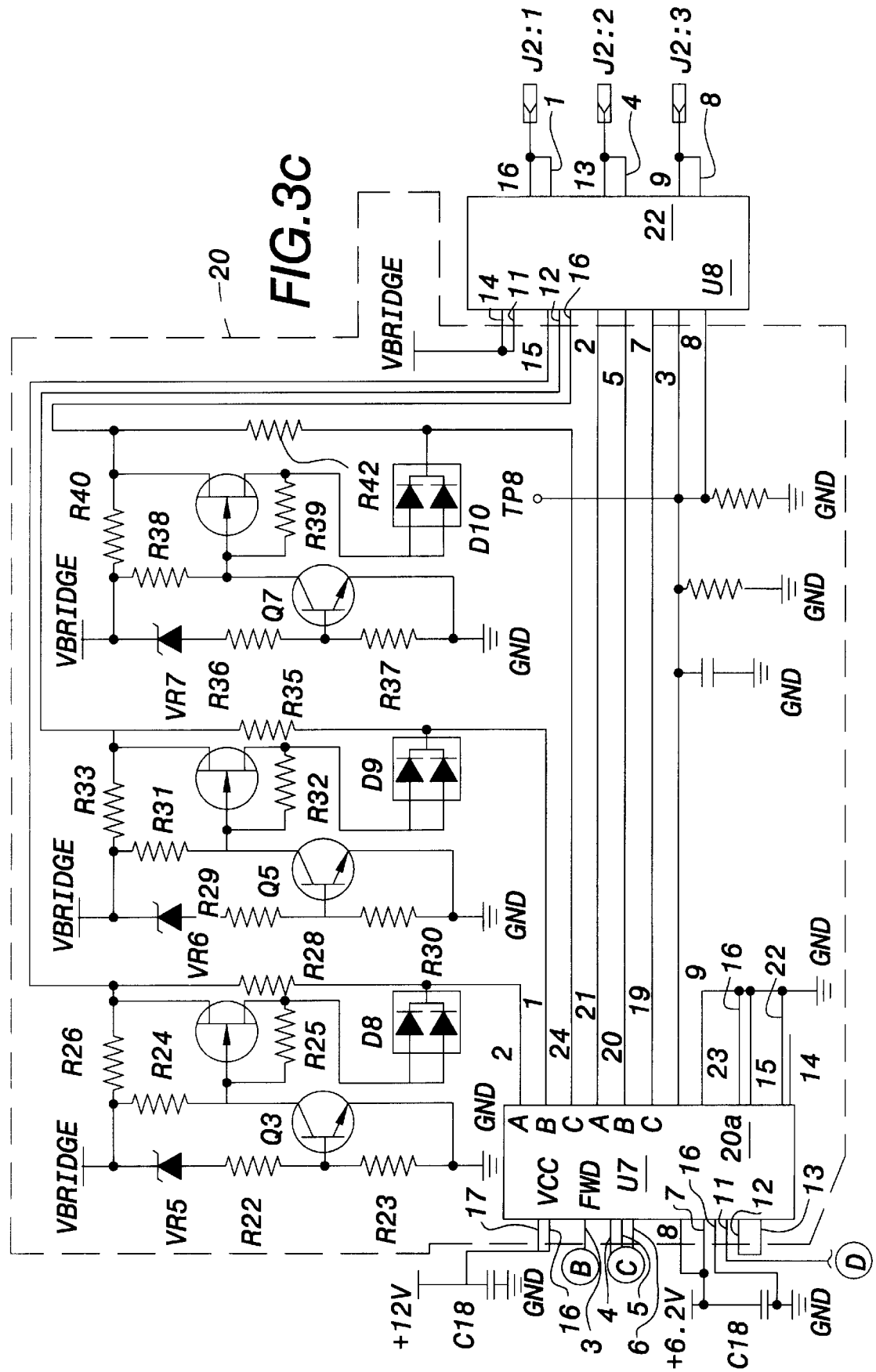

Three-phase motor controller chip 20a is a subset of the three-phase motor controller electronic circuitry identified generally as 20 in the schematic in FIG. 3c. As noted above, three-phase MOSFET bridge 22 is implemented on a single integrated circuit chip U6 and comprises the three-phase adapter output for connection to the brushless motor through connector J2.

Figure 3D:
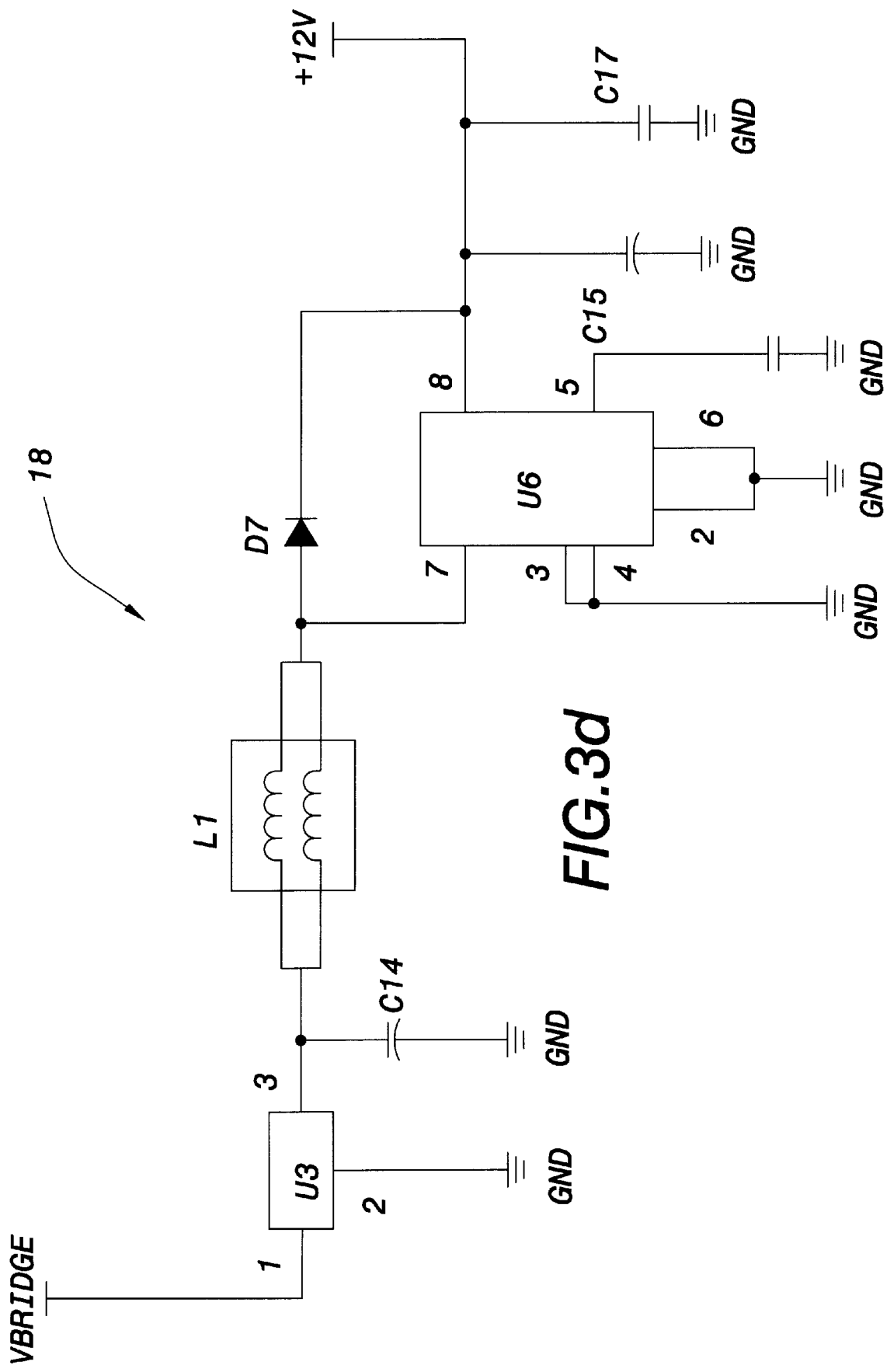

DC to DC converter 18 is illustrated in FIG. 3d and includes a connection to the output of filter 12, Vbridge, and includes a twelve volt, 500 mA LDO regulator U3 (e.g., a National Semiconductor (TM) LM2937ET-12) and a step-up DC to DC converter U6 (e.g., a Maxim (TM) MAX761CSA) to provide a regulated output of twelve volts DC (i.e., +12V).

The components of the adapter 8 are summarized in the parts list of Table 1 as follows:

TABLE I

| QTY | Part No. | Alt. Part No. | Description | Reference | Manufacturer |
|---|---|---|---|---|---|
| 1 | MBRS140T | SK14 | 40 V 1A SMT Schottky | D7 | Motrla/Diodes Inc |
| 4 | MBRS340T | SK34 | 40 V 3A SMT Schottky | D1–D4 | Motrla/Diodes Inc |
| 4 | MMBD6100LT1 | | Gen. Purpose Diode-dual, common cathode | D5, D8, D9, D10 | Motrla/Diodes Inc |
| 3 | MMBT2222ALT1 | | Gen. Purpose NPN transistor | Q3, Q5, Q7 | Motrla/Diodes Inc |
| 3 | NDS351N | | N-Ch. MOSFET | Q4, Q6, Q8 | National Semi |
| 1 | PO.51W-28K | PO.47W-28K | 0.51 ohm, 5%, 2 Watt axial resistor | R1 | Panasonic |
| 1 | 640456-2 | 22-23-2021 | 2-pin header connector w/locking ramp | J1 internal | Amp/Molex |
| 1 | 640456-8 | 22-23-2081 | 8-pin header connector w/locking ramp | J2 internal | Amp/Molex |
| 1 | RE2-34V221M | | 35 V 220 uF Alum Elec Capacitor | C1 | Elna |
| 1 | 742-083-R101CT-ND | | 100 ohm resistor array (4 isolated) | RP3 | CTS |
| 1 | 3266W-1-202 | 3296Y-1-202 | 2 k ohm trimmer, 12 or 25 turn | RT1 | Bourns |
| 1 | 742-083-R332CT-ND | | 3.3 k ohm resistor array (4 isolated) | RP6 | CTS |
| 1 | 742-163-R104CT-ND | | 100 k ohm resistor array (8 isolated) | RP2 | CTS |
| 1 | 742-163-R105CT-ND | | 1 M ohm resistor array (8 isolated) | RP1 | CTS |
| 1 | 742-083-R104CT-ND | | 100 k ohm resistor array (4 isolated) | RP5 | CTS |
| 9 | ECU-V1H104KBW | 89F5965 | 0.1 uF ceramic chip cap X7R | C3, C7, C11, C15 C17, C18, C21–23 | Panasonic/Kemet |
| 4 | ECU-V1H103KBV | | 0.01 uF ceramic chip cap X7R | C4, C5, C19, C20 | Panasonic |
| 1 | C1206C102J5GAC | 93F2368 | 1000 pF ceramic cap (NPO) | C12 | Kemet |
| 1 | TIP122 | | NPN Darlington Transistor | Q1 | Motorola |
| 3 | ECU-V1H152KBV | | 1500 pF ceramic chip cap | C8, C9, C10 | Panasonic |
| 1 | MC78L05ACD | L78L05ACD | 5 Volt Regulator | U4 | Motorola/SGS |
| 1 | LM311D | LM311N | Comparator | U1 | Motorola/TI/SGS |
| 1 | LMC6494B | LM6494A | Quad Rail-to-Rail Op Amp | U2 | National Semi |
| 1 | LM2937ET-12 | | 12 V 500 ma LDO Regulator | U3 | National Semi |
| 1 | MC33039D | | Closed Loop Motor Control IC | U5 | Motorola |
| 1 | CTX20-3P | | 20 uH | L1 | CoilTronics/GFS |
| 1 | MAX761CSA | MAX761ESA | Step-Up DC/DC Conv | U6 | Maxim |
| 1 | 293D686X96RD2T | 93F2704 | 68 uF 6.3 V Solid Tantalum Capacitor | C6 | Sprague |
| 1 | 293D685X9035D2T | 89F2727 | 6.8 uF 35 V Solid Tantalum Capacitor | C2 | Sprague |
| 2 | 293D336X9016D2T | 93F2693 | 33 uF Solid Tantalum Capacitor 25 V (16 V) | C14, C16 | Sprague |
| 1 | MC33035DW | | Brushless Motor Control IC | U7 | Motorola |
| 1 | LM4040E1M3-2.5-ND | | 2.5 V reference | U9 | National Semi |
| 1 | NDM3000 | | | | |
| 1 | LR2512R100F | | 3-Phase MOSFET Bridge | U8 | National Semi |
| 1 | CRCW 1206 622 J | 96F7809 | 0.1 ohm 1 W Sense resistor | R13 | IRC |
| 1 | RT1 | | 6.2 K Film Resistor, ⅛ W, 5% | R4 | Dale |
| 3 | CRCW 1206 102 J RT1 | | 1 K Film Resistor, ⅛ W, 5% | R26, R33, R40 | Dale |
| 3 | CRCW 1206 681 J RTI | | 680 ohm Film Resistor, ⅛ W, 5% | R28, R35, R42 | Dale |
| 1 | CRCW 0603 122 J RT1 | | 1.2 k ohm Film resistor, 1/16 W, 5% | R2 | Dale |
| 2 | P2.4KGCT-ND | | 2.4 k ohm Film resistor, 1/16 W, 5% | R20, R21 | Panasonic |
| 11 | CRCW 0603 103 J RT1 | | 10 k ohm Film resistor, 1/16 W, 5% | R18–19, R22–R24, R29–R31, R36–R38 | Dale Dale |
| 1 | P10.0kHCT-ND | | 10 k ohm Film resistor, 1/16 W, 1% | R15 | Panasonic |
| 1 | P7.5kGCT-ND | | 7.5 k ohm Film resistor, 1/16 W, 5% | R9 | Dale |
| 3 | P51kGCT-ND | | 51 K ohm Film resistor, 1/16 W, 5% | R25, R32, R39 | Dale |
| 1 | P75kHCT-ND | | 75 K ohm Film resistor, 1/16 W, 1% | R16 | Dale |
| 1 | P150kGCT-ND | | 150 k ohm Film resistor, 1/16 W, 5% | R14 | Dale |
| 1 | P200kHCT-ND | | 200 K ohm Film resistor, 1/16 W, 1% | R8 | Dale |
| 1 | BZX84C27LT1 | BZX84C27DICT-ND | 27 V zener SMT | VR1 | Motrla/Diodes Inc |
| 3 | BZX84C4V7LT1 | BZX84C4VDICT-ND | 4.7 V zener SMT | VR2–VR4 | Motrla/Diodes Inc |
| 3 | BZX84C12LT1 | BZX84C12DICT-ND | 12 V zener SMT | VR5–VR7 | Motrla/Diodes Inc |
| | NO STUFF | | | R3, R5, R7, U10, U11 | |
| | NO STUFF | | | U12, TP1–TP10, RT2 | |
| 1 | AN-1302G | | Gray NEMA-4-Enclosure | | Bud |
| 1 | JG02 | | PWB, Hummer 1 | | United Circuits |
| 1 | JBXER2G12FCSD | EGG.2B.312.CLM | Panel mount receptacle connector-crimp pins | J2 external | JBX/Lemo |
| 1 | S102-A053-13714.7-S | | 4-pin Plug connector w/male pins | J1 external | W. W. Fischer |
| 4 | TBD | | #6 screw | | TBD |
| 4 | RN-6-375A | | ¼" O.D. nylon spacer ⅜"; #6 screw | | SPC Tech |
| 1 | 3203 | | Cable, 26 awg, 4-conductor, shielded, gray | | Alpha |
| 1 | GCA.2S.255.LT | | Lug, Solder for 2S or 2B Lemo | | Lemo |
| 1 | TBD | | Tie wrap | | |
| 1 | SJ3551 | | Fastener, Dual Lock, black, self adhesive | | 3M |
| 1 | TBD | | Clamping Grommet-black | | Heyco |
| 1 | 640442-2 | | 2-pin 26 awg receptacle IDC connector | | Amp |
| 1 | 640441-8 | | 8-pin 24 awg receptacle IDC connector | | Amp |

The embodiment of FIGS. 3a–3d and the parts list of Table 1 are merely examples; a person of ordinary skill in the art will recognize that modifications and substitutions can be made.

In operation, the NPN darlington transistor Q1 of filter 12 transmits the entire adapter input voltage (as V bridge) to the P channel MOSFETS in the three-phase motor controller 20a (of FIG. 3c) and output drive stage 22 when the adapter input signal voltage is twelve volts or below but reduces the gate-to-source voltage ($V_{gs}$) to a resistor ratio (e.g., R26/R28) when the adapter input exceeds twelve volts DC, due to operation of a voltage sensing circuit including zener diodes (e.g., VR5) in motor controller 20. The P channel FETs are internally connected to pins 2,1 and 24 of controller chip 20a (i.e., U7). Using one section of circuit 20 as an example, when Vbridge is above a selected threshold level (e.g., twelve volts) zener diode VR5 is conductive, transistor Q3 is switched off and FET Q4 is off, so Vbridge is reduced across the series combination of R26 and R28 connected to pin 2 of controller chip 20a. However, when Vbridge is below twelve volts, zener diode VR5 is non-conductive, transistor Q3 is switched on, FET Q4 is on and effectively short circuits R28 so Vbridge is reduced across only R26 connected in series to pin 2 of controller chip 20a. The operation of controller 20 thus allows optimum efficiency when operating with low input voltages but limits $V_{gs}$ (e.g. at pins 2,1, and 24 of chip 20a) to under 20 volts for the range of input voltages up to 30 volts, thereby protecting the P channel MOSFETs in the output stage of controller 20. Such protection is required since the maximum rating of MOSFET $V_{gs}$ is typically twenty volts or less.

Adapter 8 accepts bipolar drive signals over the J1 inputs MTR+ and MTR– and reverses the brushless DC motor direction in response to a change of input voltage polarity from the two-wire medical console controller circuit input at J1. The adapter circuit 8 eliminates the need for a negative supply voltage by creating a positive bias in the control loop such that the control signal is nominally 2.5V above ground (i.e., the level of the RTN output of filter 12). Positive bias or offset is provided by the reference voltage circuit 16b in summer circuit 16c (as shown in FIG. 3b) and bipolar drive signal generation without a negative voltage supply. Op-Amp 16a in speed control circuit 16 has a non-inverting input connected via half bridge 16d as illustrated in FIG. 1 and FIGS. 3a and 3b (by traversing connection A), thereby forming a speed or velocity control loop for motor controller adapter 8.

Turning now to FIGS. 4a and 4b, there is illustrated a surgical instrument handpiece 70 having an interior cavity 71 within which brushless motor 72 is removably disposed. Brushless motor 72 drives a surgical implement (e.g., a burr or blade for use in ENT surgery or the like) detachably attached at the handpiece distal end 75. As illustrated in FIG. 4b, handpiece 70 includes, at its proximal end 73 a handpiece connector 74 removably attached to a distal cable connector 78 affixed to a flexible cable 76 for receiving a handpiece brushless motor driving signal as an input from the adapter 8. Opposite distal cable connector 78 and affixed to cable 76 is proximal cable connector plug 80 removably connected to electrical connector J2external of adapter 8. Mating connectors (80 and J2external) include cable connector plug 80 with twelve conductive elongate pins slidably, rectilinearly received within the conductive pin receiving sockets J2-1 through J2-12. The conductive pins of plug 80 are slidably received (with a friction conductive fit) in the pin receiving sockets 120 of output connector J2 external, thereby providing a sterile and fluid-tight seal to the electrical connection made thereby.

The adapter 8 of the present invention permits use of a handpiece (e.g., 70) having a brushless D.C. motor driving a surgical implement with a medical console 9 of the type designed for connection to brushes in a commutated D.C. motor and, thus, provides new uses for existing consoles. Accordingly, a method according to the present invention includes the steps of coupling adapter 8 to medical console 9 of the type having a two-wire controller for connection to brushes in a commutated D.C. motor, connecting an output of the adapter to a brushless D.C. motor in a handpiece for driving a surgical implement and controlling operation of the surgical handpiece via the medical console. Optionally, an operator may adjust the "full speed gain" voltage through adjustable resistor RT1 and "start speed offset" voltage through adjustable resistor RT2, to calibrate the operating speed of the instrument motor for use with a given medical console.

Having described preferred embodiments of a new and improved adapter and circuit, it is believed that other modifications, variations and changes will be suggested to those skilled in the art in view of the teaching set forth herein. It is therefore to be understood that all such variations, modifications and changes are believed to fall within the scope of the present invention as defined by the appended claims.

What is claimed is:

1. An electrical adapter for driving a surgical instrument brushless motor, comprising:
   a first electrical connection to receive a first motor control signal and a second motor control signal having a polarity opposite said first motor control signal;
   a direction sensing circuit responsive to said first motor control signal and said second motor control signal to generate a direction signal;
   an internal circuit to convert power received from at least one of said first motor control signal or said second motor control signal into a selected supply rail voltage and a return rail voltage;
   a speed sensing circuit responsive to said first motor control signal and said second motor control signal to generate a speed signal;
   a brushless motor controller circuit responsive to said direction signal and said speed signal to generate a brushless motor control signal.

2. The electrical adapter of claim 1, wherein said brushless motor controller circuit receives said selected supply rail voltage.

3. The electrical adapter of claim 1, wherein said brushless motor controller circuit comprises a three-phase motor controller circuit and a three-phase bridge circuit.

4. The electrical adapter of claim 1, further including a housing having an interior volume, wherein said direction sensing circuit, said internal power supply circuit, said speed sensing circuit and said brushless motor controller circuit are disposed within said interior volume.

5. The electrical adapter of claim 4, further including a first electrical connector and a second electrical connector;
   wherein said first electrical connector is selectively connectable to said first electrical connection for receiving a first motor control signal and second motor control signal; and
   wherein said second electrical connector is selectively connectable to a surgical instrument including a brushless motor to provide said brushless motor control signal to a surgical instrument having a brushless motor.

6. The electrical adapter of claim 1, wherein said speed sensing circuit includes a differential amplifier having a first input connected to said selected supply voltage and a second input connected to said return voltage.

7. The electrical adapter of claim 1, wherein said three-phase motor controller circuit generates an accessory speed control signal in response to said speed signal.

8. The electrical adapter of claim 7, wherein said three-phase motor controller circuit accessory speed control signal is a pump speed control signal.

9. The electrical adapter of claim 1, further including a housing having an interior volume, wherein said direction sensing circuit, said internal power supply circuit, said speed sensing circuit and said brushless motor controller circuit are disposed within said interior volume.

10. The electrical adapter of claim 9, further including a first electrical connector and a second electrical connector;

wherein said first electrical connector is selectively connectable to said first electrical connection for receiving a first motor control signal and second motor control signal; and wherein said second electrical connector is selectively connectable to the instrument to provide said brushless motor control signal to the brushless motor.

11. The electrical adapter of claim 1, wherein said brushless motor controller circuit includes a voltage sensing circuit;

wherein said voltage sensing circuit detects whether said supply signal exceeds a selected threshold and attenuates said supply voltage in response thereto.

12. In combination, a surgical instrument having a brushless D.C. motor driving a surgical implement and an input for receiving drive signals for said brushless D.C. motor, and a controller adapter comprising a first electrical connection to receive a first motor control signal and a second motor control signal having a polarity opposite said first motor control signal; a direction sensing circuit responsive to said first motor control signal and said second motor control signal to generate a direction signal; an internal power supply circuit to convert power received from at least one of said first motor control signal or said second motor control signal into a selected supply voltage; a speed sensing circuit responsive to said first motor control signal and said second motor control signal to generate a speed signal; and a brushless motor controller circuit responsive to said direction signal and said speed signal to generate a brushless motor drive signal.

13. A method for controlling a surgical instrument having a brushless motor with a controller having a bipolar, two-wire output, comprising:

sensing the polarity of the control signal provided by the bipolar, two-wire output;

sensing the amplitude of the control signal provided by the bipolar, two-wire output; and generating a brushless motor control signal in response to the sensed polarity and amplitude of the bipolar, two-wire output.

14. The method of claim 13, wherein said step of generating a brushless motor control signal includes generating drive signals for a first, second and third phase.

15. The method of claim 13, wherein said step of generating a brushless motor control signal includes sensing brushless motor speed and generating a brushless motor speed control signal in response thereto.

16. In combination, a surgical instrument adapted to receive and drive surgical implements with a handpiece including a brushless motor, said instrument being connected to an electrical adapter comprising a first electrical connection to receive a first motor control signal and a second motor control signal having a polarity opposite said first motor control signal; a direction sensing circuit responsive to said first motor control signal and said second motor control signal to generate a direction signal; an internal power supply circuit to convert power received from at least one of said first motor control signal a said second motor control signal into a supply voltage; a speed sensing circuit responsive to said first motor control signal and said second motor control signal to generate a speed signal; and a brushless motor controller circuit responsive to said direction signal and said speed signal to generate a brushless motor control signal; wherein said brushless motor control signal is an adapter output transmitted to said handpiece via an electrical connector including a plurality of pin receiving sockets.

17. A method of operating a surgical instrument of the type having a handpiece housing a brushless D.C. motor arranged to drive a surgical implement comprising the steps of:

coupling an input of an electrical adapter with an output of a medical console providing at the output a two-wire bipolar output signal, the electrical adapter including an output and electrical circuitry producing a drive signal at the output thereof for controlling a brushless D.C. motor;

coupling the handpiece to the output of the electrical adapter; and controlling the operation of the surgical instrument via the medical console.

18. The method of claim 17, further comprising:

calibrating the operating speed of the surgical instrument motor for use with a given medical console.

19. The method of claim 18, wherein said calibrating step includes adjusting the adapter speed gain and speed offset.

* * * * *